US007002057B2

(12) United States Patent
Allen et al.

(10) Patent No.: US 7,002,057 B2
(45) Date of Patent: Feb. 21, 2006

(54) THIOREDOXIN H HOMOLOGS

(75) Inventors: Stephen M. Allen, Wilmington, DE (US); John D. Everard, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/978,538

(22) Filed: Nov. 1, 2004

(65) Prior Publication Data

US 2005/0221345 A1    Oct. 6, 2005

Related U.S. Application Data

(62) Division of application No. 09/786,715, filed as application No. PCT/US99/20420 on Sep. 7, 1999, now Pat. No. 6,897,356.

(60) Provisional application No. 60/099,501, filed on Sep. 8, 1998.

(51) Int. Cl.
    *C07H 21/04*      (2006.01)
    *A01H 1/00*       (2006.01)
    *C12N 15/29*      (2006.01)
    *C12N 5/14*       (2006.01)
    *C12P 21/02*      (2006.01)

(52) U.S. Cl. ...................... 800/278; 800/298; 435/69.1; 435/235.1; 435/252.3; 435/254.11; 435/320.1; 435/325; 435/410; 536/23.1

(58) Field of Classification Search ...................... None
    See application file for complete search history.

(56) References Cited

U.S. PATENT DOCUMENTS

5,777,200 A    7/1998    Ryals et al.

FOREIGN PATENT DOCUMENTS

| WO | WO 93/08274    | 4/1993 |
| WO | WO 95/19443    | 7/1995 |
| WO | WO 96/03505 A1 | 2/1996 |
| WO | WO 96/12799    | 5/1996 |

OTHER PUBLICATIONS

Renata Rivera-Madrid et al., Plant Phys., vol. 102:327-328, 1993, Nucleotides sequence of a cDNA clone encoding an *Arabidopsis thaliana* Thioredoxin h.
Renata Rivera-Madrid et al., PNAS, vol. 92:5620-5624, 1995, Evidence for five divergent thioredoxin h sequences in *Arabidopsis thaliana*.
Sabelle Marty et al., Plant Mol. Biol., vol. 17:143-147, 1991, Nucleotide sequence of a cDNA encoding a tobacco thioredoxin.
EMBL Database Sequence Library Accession No.: Z70677, Apr. 4, 1996, Szederkenyi, J. et al., cDNA expressed in *Ricinus cotyledons*.
Christophe Brugidou et al., Mol. Gen. Genet., vol. 238:285-293, 1993, The *Nicotiana tabacum* genome encodes two cytoplasmic thioredoxin genes which are differently expressed.
Jinrui Shi et al., Plant Mol. Biol., vol. 32:653-662, 1996, A novel plasma membrane-bound thioredoxin from soybean.
Bob B. Buchanan et al., Arch. of Biochem. & Biophys., vol. 314(2):257-260, 1994, Thioredoxin: A multifunctional regulatory protein with a bright future in Technology and Medicine.
Marie-Francoise Gautier et al., Eur. J. Biochem., vol. 252: 314-324, 1998, Characterization of wheat thioredoxin h cDNA and production of an active *Triticum aestivum* protein in *Escherichia coli*.
Kayo Maeda et al., Eur. J. Biochem., vol. 154:197-203, 1986, Future characterization and amino acid sequence of m-type thioredoxins from spinach chloroplasts.
EMBL Database Sequence Library Accession No.: AI736736, Jun. 18, 1999, Shoemaker, R. et al., Public Soybean EST Project.
Arne Holmgren, Ann. Rev. Biochem., vol. 54:237-271, 1985, Thioredoxin.
Arne Holmgren, Curr. Biol., vol. 3:239-243, 1995, Thioredoxin structure and mechanism: conformational changes on oxidation of the active-site sulfhydryls to a disulfide.
National Center for Biotechnology Information General Identifier No. 267122, Oct. 1, 2000, Rivera-Madrid, R. et al., Nucleotide sequence of a cDNA clone encoding and *Arabidopsis thaliana* thioredoxin h.
Mariam Sahrawy et al., J. Mol. Evol., vol. 42:422-431, 1996, Intron position as an evolutionary marker of thioredoxins and thioredoxin domains.
National Center for Biotechnology Information General Identifier No. 267124, Accession No. P29449, Oct. 1, 2000, Marty, I. et al., Nucleotide sequence of a cDNA encoding a tobacco thioredoxin.
National Center for Biotechnology Information General Identifier No. 1255954, Accession No. CAA94534, Apr. 4, 1996, Szederkenyi, J. et al., cDNA Expressed in *Ricinus cotyledons*.
National Center for Biotechnology Information General Identifier No. P29448, Accession No. CAA47694, P. Nedellec et al., Characterization of the human biliary glycoprotein regulatory region, Oct. 1, 2000.

Primary Examiner—Robert A. Wax

(57) ABSTRACT

This invention relates to an isolated nucleic acid fragment encoding a thioredoxin protein. The invention also relates to the construction of a chimeric gene encoding all or a portion of the thioredoxin protein, in sense or antisense orientation, wherein expression of the chimeric gene results in production of altered levels of the thioredoxin protein in a transformed host cell.

14 Claims, No Drawings

THIOREDOXIN H HOMOLOGS

This application is a division of U.S. application Ser. No. 09/786,715 filed Mar. 7, 2001 now U.S. Pat. No. 6,897,356, which is a National Stage Application of PCT/US/99/20420 filed on Sep. 7, 1999 which claims the benefit of U.S. Provisional Application No. 60/099,501, filed Sep. 8, 1998.

FIELD OF THE INVENTION

This invention is in the field of plant molecular biology. More specifically, this invention pertains to nucleic acid fragments encoding thioredoxin proteins in plants and seeds.

BACKGROUND OF THE INVENTION

Thioredoxin H is a cytosolic member of the thioredoxin family of proteins. These small proteins (typical mass of 12 kD) have been shown to play a central role in the activation of proteins by influencing the redox status of sulfhydryl groups on target proteins (Holmgren et al. (1985) *Annu. Rev. Biochem* 54:237–271; and Holmgren et al. (1995) *Structure* 3(3):239–243). Two other thioredoxin classes, F and M, are located in plastids and have been shown to be involved in redox mediated activation/inactivation of various photosynthetic enzymes during light/dark transitions. The cytosolic (H) form of thioredoxin has been shown to be involved in disassembly of seed storage proteins during germination and in the bread making process. In the former case storage proteins are held together in clusters by S—S bonds. On germination thioredoxin H reduces the S—S bonds and the subunits dissociate, facilitating attack by proteases. During bread making the same processes occur. Reduction of the S—S bonds causes the protein complexes to disassemble allowing them to be distributed through out the dough during mixing. During kneading the S—H bonds become oxidized and start to reassociate in a random manner, the cross linked matrix formed by this process entraps $CO_2$ formed during yeast fermentation and is responsible for the raising process. Addition of thioredoxin H to poor quality flours improves their quality for the production of bread.

Thioredoxin H has also been shown to inactivate snake and bee venom toxins and has been shown to reduce the allergenicity of cereal proteins. In the later, the process is presumably the same as described above; by reducing the S—S bonds holding the storage protein clusters together they are more susceptible to denaturation and proteolysis in the gut. Thioredoxin H may also be overexpressed in transformed corn kernels and other cereal crops. The wet milling industry, which is primarily focused on starch extraction, steeps corn in liquors of sodium metabisulphite or $SO_2$. Although this has many secondary effects (e.g., suppression of microbial activity), the primary function is to cause a dissociation of the storage proteins which leads to more efficient starch extraction. Small increases in extractable starch translate into significant increases in the profit margins for the wet millers. By overexpressing thioredoxin H in maize kernels and other cereals it may possible to improve starch recoveries, reduce steep times, and reduce or eliminate the use of sulfur compounds in the steeping process. Overexpression of thioredoxin H in maize kernels and other cereals may have the added advantage of reducing the allergenicity of any transgenic protein engineered into cereal crops with high sulfhydryl content.

SUMMARY OF THE INVENTION

The present invention relates to isolated polynucleotides comprising a nucleotide sequence encoding a first polypeptide of at least 100 amino acids that has at least 80% identity based on the Clustal Method of alignment when compared to a polypeptide selected from the group consisting of a *Momordica charantia* thioredoxin polypeptide of SEQ ID NO:2, a *Catakoa speciosa* thioredoxin polypeptide of SEQ ID NO:4, a soybean thioredoxin polypeptide of SEQ ID NO:6, a soybean thioredoxin polypeptide of SEQ ID NO:8, and a *Vernonia* thioredoxin polypeptide of SEQ ID NO: 10. The present invention also relates to an isolated polynucleotide comprising the complement of the nucleotide sequences described above. It is preferred that the isolated polynucleotides of the claimed invention consists of regions of the isolated polynucleotide selected from the group SEQ ID NO: 1, 3, 5, 7 and 9 that codes for the polypeptide selected from the group consisting of SEQ ID NO:2, 4, 6, 8 and 10. The present invention also relates to an isolated polynucleotide comprising a nucleotide sequences of at least one of 40 (preferably 30) contiguous nucleotides derived from a nucleotide sequence selected from the group consisting of SEQ ID NO: 1, 3, 5, 7, 9 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eucaryotic, such as a yeast or a plant cell, or procaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene or isolated polynucleotide of the present invention, the process comprising either transforming or transfecting an isolated compatible host cell with a chimeric gene or isolated polynucleotide of the present invention.

The present invention relates to a thioredoxin polypeptide of at least 100 amino acids comprising at least 80% homology based on the Clustal method of alignment compared to a polypeptide selected from the group consisting of SEQ ID NO:2, 4, 6, 8 and 10.

The present invention relates to a method of selecting an isolated polynucleotide that affects the level of expression of a thioredoxin polypeptide in a plant cell, the method comprising the steps of:

constructing an isolated polynucleotide or chimeric gene of the present invention;

introducing the isolated polynucleotide into a plant cell;

measuring the level of thioredoxin polypeptide in the plant cell containing the polynucleotide; and comparing the level of thioredoxin polypeptide in the plant cell containing the isolated polynucleotide with the level of thioredoxin polypeptide in a plant cell that does not contain the isolated polynucleotide.

The present invention relates to a method of obtaining a nucleic acid fragment encoding a substantial portion of a thioredoxin gene, preferably a plant thioredoxin gene, comprising the steps of: synthesizing an oligonucleotide primer comprising a nucleotide sequence of at least one of 40 (preferably 30) contiguous nucleotides derived from a nucleotide sequence selected from the group consisting of SEQ ID NO: 1, 3, 5, 7, 9 and the complement of such nucleotide sequences; and amplifying a nucleic acid fragment (preferably a cDNA inserted in a cloning vector) using the oligonucleotide primer. The amplified nucleic acid fragment preferably will encode a portion of a thioredoxin polypeptide amino acid sequence.

The present invention also relates to a method of obtaining a nucleic acid fragment encoding all or a substantial portion of the amino acid sequence encoding a thioredoxin protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Thioredoxin Proteins

| | | SEQ ID NO: | |
|---|---|---|---|
| Protein | Clone Designation | (Nucleotide) | (Amino Acid) |
| Thioredoxin H | fds.pk0001.e9 | 1 | 2 |
| Thioredoxin H | ncs.pk0010.e3 | 3 | 4 |
| Thioredoxin H | sah1c.pk001.l17 | 5 | 6 |
| Thioredoxin H | sfl1.pk0029.e2 | 7 | 8 |
| Thioredoxin H | vs1n.pk0012.f3 | 9 | 10 |

The Sequence Listing contains the one letter code for nucleotide sequence characters and the three letter codes for amino acids which is in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, a polynucleotide comprising a nucleotide sequence of at least one of 40 (preferably 30) contiguous nucleotides derived from a nucleotide sequence selected from the group consisting of SEQ ID NO: 1, 3, 5, 7, 9 and the complement of such nucleotide sequences may be used in methods of selecting an isolated polynucleotide that affects the expression of a thioredoxin polypeptide in a plant cell.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (polynucleotides) encode amino acid sequences that are 80% identical to the amino acid sequences reported herein. Preferred nucleic acid fragment encode amino acid sequences that are 85% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993)*J. Mol. Biol* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several thioredoxin proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other thioredoxin H proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 40 (preferably 30) contiguous nucleotides derived from a nucleotide sequence selected from the group consisting of SEQ ID NO: 1, 3, 5, 7, 9 and the complement of such nucleotide sequences may be used in such methods to obtain a nucleic acid fragment encoding a substantial portion of an amino acid sequence of a thioredoxin polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of thioredoxin activity in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded thioredoxin protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various barley, Catalpa, pear, soybean and Vernonia tissues were prepared. The characteristics of the libraries are described below.

TABLE 2 cDNA Libraries from Barley, Catalpa, Pear, Soybean and Vernonia

| Library | Tissue | Clone |
|---|---|---|
| fds | *Momordica charantia* developing seed | fds.pk0001.e9 |
| ncs | *Catalpa speciosa* developing Seed | ncs.pk0010.e3 |
| sah1c | Soybean sprayed with Authority herbicide. | sah1c.pk001.l17 |
| sfl1 | Soybean immature flower | sfl1.pk0029.e2 |
| vs1n | Vernonia Seed* | vs1n.pk0012.f3 |

*This library was normalized essentially as described in U.S. Pat. No. 5,482,845, incorporated herein by reference.

cDNA clones encoding thioredoxin proteins were identified by conducting BLAST (Basic Local Alignment Search Tool; Altschul et al. (1993) *J. Mol. Biol* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 2

Identification of cDNA Clones cDNA clones encoding thioredoxin proteins were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Thioredoxin H

The BLASTX search using the EST sequences from clones listed in Table 3 revealed similarity of the polypeptides encoded by the cDNAs to thioredoxin H from *Arabidopsis thaliana* (NCBI Identifier No. gi 267122), *Nicotiana tabacum* (NCBI Identifier No. gi 267124) and *Ricinus communes* (NCBI Identifier No. gi 1255954). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Arabidopsis thaliana*, *Nicotiana tabacum* and *Ricinus communis* Thioredoxin H

| Clone | Status | BLAST pLog Score |
|---|---|---|
| fds.pk0001.e9 | FIS | 35.50 (gi 267122) |
| ncs.pk0010.e3 | FIS | 48.40 (gi 267124) |
| sah1c.pk001.l17 | FIS | 49.00 (gi 1255954) |
| sfl1.pk0029.e2 | FIS | 41.00 (gi 1255954) |
| vs1n.pk0012.f3 | FIS | 41.70 (gi 267124) |

The data in Table 4 represents a calculation of the percent identity of the amino acid sequences set forth in SEQ ID NOs:2, 4, 6, 8 and 10 and the *Arabidopsis thaliana*, *Nicotiana tabacum* and *Ricinus* communes sequences (SEQ ID NOs:11, 12 and 13 respectively). The percent identity between the amino acid sequences set forth in SEQ ID NOs:2, 4, 6, 8 and 10 ranged from 49% to 80%.

TABLE 4

Percent Identity of Amino Acid Sequences Deduced From the Nucleotide Sequences of cDNA Clones Encoding Polypeptides Homologous to *Arabidopsis thaliana*, *Nicotiana tabacum* and *Ricinus communis* Thioredoxin H

| SEQ ID NO. | Percent Identity to |
|---|---|
| 2 | 62% (gi 267122) |
| 4 | 75% (gi 267124) |
| 6 | 75% (gi 1255954) |
| 8 | 65% (gi 1255954) |
| 10 | 69% (gi 267124) |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a thioredoxin H. These sequences represent the first Catalpa, pear, soybean and Vernonia sequences encoding thioredoxin H.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embroys may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al.(1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/nL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenouchloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having thioredoxin h activity, wherein the polypeptide has an amino acid sequence of at least 80% sequence identity, based on the Clustal V method of alignment, when compared to SEQ ID NO:8, or
   (b) a full-length complement of the nucleotide sequence of (a).

2. The polynucleotide of claim 1, wherein the amino acid sequence of the polypeptide has at least 85% sequence identity, based on the Clustal V method of alignment, when compared to SEQ ID NO:8.

3. The polynucleotide of claim 1, wherein the amino acid sequence of the polypeptide has at least 90% sequence identity, based on the Clustal V method of alignment, when compared to SEQ ID NO:8.

4. The polynucleotide of claim 1, wherein the amino acid sequence of the polypeptide has at least 95% sequence identity, based on the Clustal V method of alignment, when compared to SEQ ID NO:8.

5. The polynucleotide of claim 1, wherein the amino acid sequence of the polypeptide comprises SEQ ID NO:8.

6. The polynucleotide of claim 1 wherein the nucleotide sequence comprises SEQ ID NO:7.

7. A vector comprising the polynucleotide of claim 1.

8. A recombinant DNA construct comprising the polynucleotide of claim 1 operably linked to at least one regulatory sequence.

9. A method for transforming a cell, comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

14. A virus comprising the recombinant DNA construct of claim 8.

* * * * *

SEQUENCE LISTING

<160> NUMBER OF SEQ ID NOS: 150

<210> SEQ ID NO 1
<211> LENGTH: 1518
<212> TYPE: DNA
<213> ORGANISM: Artificial Sequence
<220> FEATURE:
<223> OTHER INFORMATION: Codon-Optimized HPV16 L1

<400> SEQUENCE: 1

```
atgagcctgt ggctgcccag cgaggccacc gtgtacctgc ctcccgtgcc cgtgagcaag      60
gtggtgagca ccgacgagta cgtggcccgc accaacatct actaccacgc cggcaccagc     120
cgcctgctgg ccgtgggcca ccctacttc cccatcaaga agcccaacaa caacaagatc      180
ctggtgccca aggtgagcgg cctgcagtac cgcgtgttcc gcatccacct gcccgacccc    240
aacaagttcg gcttccccga cacaagcttc tacaacccg acacccagcg cctggtgtgg     300
gcctgcgtgg gcgtggaggt gggccgcggc cagcccctgg gcgtgggcat cagcggccac   360
cccctgctga acaagctgga cgacaccgag aacgccagcg cctacgccgc caacgccggc   420
gtggacaacc gcgagtgcat cagcatggac tacaagcaga cccagctgtg cctgatcggc   480
tgcaagcctc ccatcggcga gcactggggc aagggcagcc cctgcaccaa cgtggccgtg   540 aacccggcg actgccctcc cctggagctg atcaacaccg tgatccagga cggcgacatg   600
gtggacaccg gcttcggcgc catggacttc accaccctgc aggccaacaa gagcgaggtg   660
cccctggaca tctgcaccag catctgcaag tacccggct acatcaagat ggtgagcgag    720
ccctacggcg acagcctgtt cttctacctg cgccgcgagc agatgttcgt gcgccacctg   780
ttcaaccgcg ccggcgccgt gggcgagaac gtgcccgacg acctgtacat caagggcagc   840
ggcagcaccg ccaacctggc cagcagcaac tacttcccca ctcccagcgg cagcatggtg   900
accagcgacg cccaaatctt caacaagccc tactggctgc agcgcgccca gggccacaac   960
aacggcatct gctgggggcaa ccagctgttc gtgaccgtgg tggacaccac ccgcagcacc   1020
aacatgagcc tgtgcgccgc catcagcacc agcgagacca cctacaagaa caccaacttc    1080
aaggagtacc tgcgccacgg cgaggagtac gacctgcagt tcatcttcca gctgtgcaag    1140 atcacccctga ccgccgacgt gatgacctac atccacagca tgaacagcac catcctggag   1200
```

```
gactggaact tcggcctgca gccccctccc ggcggtaccc tggaggacac ctaccgcttc    1260
gtgaccagcc aggccatcgc ctgccagaag cacacccctc ccgctcccaa ggaggatccc    1320
ctgaagaagt acaccttctg ggaggtgaac ctgaaggaga agttcagcgc cgacctggac    1380
cagttccccc tgggccgcaa gttcctgctg caggccggcc tgaaggccaa gcccaagttc    1440
accctgggca gcgcaaggc caccccacc accagcagca ccagcaccac cgccaagcgc    1500
aagaagcgca agctgtaa                                                  1518

<210> SEQ ID NO 2
<211> LENGTH: 1950
<212> TYPE: DNA
<213> ORGANISM: Artificial Sequence
<220> FEATURE:
<223> OTHER INFORMATION: Mutant, Codon-Optimized HPV16 E1

<400> SEQUENCE: 2
atggccgacc ccgccggcac caacggcgag gagggcaccg gctgcaacgg ctggttctac      60
gtggaggccg tggtggagaa gaagaccggc gacgccatca gcgacgacga gaacgagaac     120
gacagcgaca ccggcgagga cctggtggac ttcatcgtga cgacaacga ctacctgacc      180 caggccgaga ccgagaccgc ccacgccctg ttcaccgccc aggaggccaa gcagcaccgc     240
gacgccgtgc aggtgctgaa gcgcaagtac ctgggcagcc ccctgagcga catcagcggc     300
tgcgtcgaca caacatcag ccccgcctg aaggccatct gcatcgagaa gcagagccgc       360
gccgccaagc gccgcctgtt cgagagcgag gacagcggc acggcaacac cgaggtggag     420
acccagcaga tgctgcaggt ggagggccgc cacgagaccg agacccctg cagccagtac      480 agcggcggca gcggcggcgg ctgcagccag tacagcagcg gcgcggcgg cgagggcgtg     540 agcgagcgcc acaccatctg ccagaccct ctgaccaaca tcctgaacgt gctgaagacc      600
agcaacgcca aggccgccat gctggccaag ttcaaggagc tgtacggcgt gagcttcagc     660
gagctggtgc gccccttcaa gagcaacaag agcacctgct gcgactggtg catcgccgcc     720
ttcggcctga ccccagcat cgccgacagc atcaagaccc tgctgcagca gtactgcctg      780
tacctgcaca tccagagcct ggcctgcagc tggggcatgg tggtgctgct gctggtgcgc     840
tacaagtgcg gcaagaaccg cgagaccatc gagaagctgc tgagcaagct gctgtgcgtg     900
agccccatgt gcatgatgat cgagcctccc aagcttcgca gcaccgccgc cgccctgtac     960
tggtacaaga ccggcatcag caacatcagc gaggtgtacg gcgacacccc cgagtggatc    1020
cagcgccaga ccgtgctgca gcacagcttc aacgactgca ccttcgagct gagccagatg    1080
gtgcagtggg cctacgacaa cgacatcgtg gacgacagcg agatcgccta caagtacgcc    1140
cagctggccg acaccaacag caacgccagc gccttcctga gagcaacag ccaggccaag    1200 atcgtgaagg actgcgccac catgtgccgc cactacaagc gcgccgagaa gaagcagatg    1260
agcatgagcc agtggatcaa gtaccgctgc gaccgcgtgg acgacggcgg cgaccgcaag    1320
cagatcgtga tgttcctgcg ctaccagggc gtggaattca tgagcttcct gaccgccctg    1380
aagcgcttcc tgcagggcat ccccaagaag aactgcatcc tgctgtacgg cgccgccaac    1440
accgacaaga gcctgttcgg catgagcctg atgaagttcc tgcagggcag cgtgatctgc    1500
ttcgtgaaca gcaagagcca cttctggctg cagcccctgg ccgacgccaa gatcggcatg    1560
ctggacgacg ccaccgtgcc ctgctggaac tacatcgacg acaacctgcg caacgccctg    1620
gacggcaacc tggtgagcat ggacgtgaag caccgccccc tggtgcagct gaagtgccct    1680
```

```
ccctgctga tcaccagcaa catcaacgcc ggcaccgaca gccgctggcc ctacctgcac   1740
aaccgcctgg tggtgttcac cttccccaac gagttcccct cgacgagaa cggtaacccc   1800 gtgtacgagc tgaacgacaa gaactggaag agcttcttca gccgcacctg agccgcctg   1860 agcctgcacg aggacgagga caaggagaac gacggcgaca gcctgcccac cttcaagtgc   1920
gtgagcggcc agaacaccaa caccctgtaa                                    1950

<210> SEQ ID NO 3
<211> LENGTH: 1098
<212> TYPE: DNA
<213> ORGANISM: Artificial Sequence
<220> FEATURE:
<223> OTHER INFORMATION: Mutant, Codon-Optimized HPV16 E2

<400> SEQUENCE: 3
atggagaccc tgtgccagcg cctgaacgtg tgccaggaca agatcctgac ccactacgag     60
aacgacagca ccgacctgcg cgaccacatc gactactgga agcacatgcg cctggcctgc   120
gccatctact acaaggcccg cgagatgggc ttcaagcaca tcaaccacca ggtggtgccc   180
accctggccg tgagcaagaa caaggccctg caggccgccg agctgcagct gaccctggag   240
accatctaca cagccagta cagcaacgag aagtggaccc tgcaggacgt gagcctggag   300
gtgtacctga ccgccccac cggctgcatc aagaagcacg gctacaccgt ggaggtgcag   360
ttcgacggcg acatctgcaa caccatgcac tacaccaact ggacccacat ctacatctgc   420
gaggaggcca gcgtgaccgt ggtggagggc caggtggact actacggcct gtactacgtg   480
cacgagggca tccgcaccta cttcgtgcag ttcaaggacg acgccgagaa gtacagcaag   540
aacaaggtgt gggaggtgca cgccggcggc caggtgatcc tgtgccccac cagcgtgttc   600
agcagcaacg aggtgagcag ccccgagacc atccgccagc cctggccaa ccacagcgcc   660 gccacccaca ccaaggccgt ggccctgggc accgaggaga cccagaccac catccagcgc   720
ccccgcagcg agcccgacac cggcaacccc tgccacacca ccaagctgct gcaccgcgac   780
agcgtggaca cgcccccat cctgaccgcc ttcaacagca gccacaaggg ccgcatcaac   840
tgcaacagca acaccacccc catcgtgcac ctgaagggcg acgccaacac cctgaagtgc   900
ctgcgctacc gcttcaagaa gcactgcaag ctgtacaccg ccgtgagcag cacctggcac   960
tggaccggcc acaacgtgaa gcacaagagc gccatcgtga ccctgaccta cgacagcgag   1020
tggcagcgcg accagttcct gagccaggtg aagatcccca gaccatcac cgtgagcacc   1080 ggcttcatga gcatctaa                                                 1098

<210> SEQ ID NO 4
<211> LENGTH: 297
<212> TYPE: DNA
<213> ORGANISM: Artificial Sequence
<220> FEATURE:
<223> OTHER INFORMATION: Mutant, Codon-Optimized HPV16 E7

<400> SEQUENCE: 4
atgcacggcg acacccccac cctgcacgag tacatgctgg acctgcagcc cgagaccacc     60
gacctgtacg gctacggcca gctgaacgac agcagcgagg aggaggacga gatcgacggc   120
cccgccggcc aggccgagcc cgaccgcgcc cactacaaca tcgtgacctt ctgctgcaag   180
tgcgacagca ccctgcgcct gtgcgtgcag agcacccacg tggacatccg cacccctggag   240 gacctgctga tgggcacccct gggcatcgtg tgccccatct gcagccagaa gccctaa       297
```

<210> SEQ ID NO 5
<211> LENGTH: 297
<212> TYPE: DNA
<213> ORGANISM: Artificial Sequence
<220> FEATURE:
<223> OTHER INFORMATION: Codon-Optimized HPV6a E7

<400> SEQUENCE: 5

```
atgcacggcc gccacgtgac cctgaaggac atcgtgctgg acctgcagcc tcccgacccc      60
gtgggcctgc actgctacga gcagctggtg acagcagcg aggacgaggt ggacgaggtg     120
gacgccagg acagccagcc cctgaagcag cacttccaga tcgtgacctg ctgctgcggc     180
tgcgacagca acgtgcgcct ggtggtgcag tgcaccgaga ccgacatccg cgaggtgcag     240
cagctcctgc tgggtaccct gaacatcgtg tgccccatct gcgctcccaa gacctaa      297
```

<210> SEQ ID NO 6
<211> LENGTH: 318
<212> TYPE: DNA
<213> ORGANISM: Artificial Sequence
<220> FEATURE:
<223> OTHER INFORMATION: Codon-Optimized HPV18 E7

<400> SEQUENCE: 6

```
atgcacggcc ccaaggccac cctgcaggac atcgtgctgc acctggagcc ccagaacgag      60
atccccgtgg acctgctgtg ccacgagcag ctgagcgaca gcgaggagga gaacgacgag     120
atcgacggcg tgaaccacca gcacctgccc gctcgcaggg ccgagcccca gcgccacacc     180
atgctgtgca tgtgctgcaa gtgcgaggcc cgcatcgagc tggtggtgga gagcagcgct     240
gacgacctgc gcgccttcca gcagctgttc ctgaacaccc tgagcttcgt gtgcccctgg     300
tgcgccagcc agcagtaa                                                   318
```

<210> SEQ ID NO 7
<211> LENGTH: 1107
<212> TYPE: DNA
<213> ORGANISM: Artificial Sequence
<220> FEATURE:
<223> OTHER INFORMATION: Codon-Optimized HPV6a E2

<400> SEQUENCE: 7

```
atggaggcca tcgccaagcg cctggacgcc tgccaggagc agctgctgga gctgtacgag      60
gagaacagca ccgacctgca aagcacgtg ctgcactgga agtgcatgcg ccacgagagc     120
gtgctgctgt acaaggccaa gcagatgggc ctgagccaca tcggcatgca ggtggtgcct     180
cctctgaagg tgagcgaggc caagggccac aacgccatcg agatgcagat gcacctcgag     240
agcctgctgc gcaccgagta cagcatggag ccctggaccc tgcaggagac cagctacgag     300
atgtggcaga ccctcccaa gcgctgcttc aagaagcgcg gcaagaccgt ggaggtgaag     360
ttcgacggct gcgccaacaa caccatggac tacgtggtgt ggaccgacgt gtacgtgcag     420
gacaacgaca cctgggtgaa ggtgcacagc atggtggacg ccaagggcat ctactacacc     480
tgtggccagt tcaagaccta ctacgtgaac ttcgtgaagg aggccgagaa gtacggcagc     540
accaagcact gggaggtgtg ctacggcagc accgtgatct gcagccccgc tagcgtgagc     600
agcaccaccc aggaggtgag catccccgag agcaccacct acactcccgc ccagaccagc     660
accctggtga gcagcagcac caaggaggac gccgtgcaga cccctcctcg caagcgcgcc     720
cgcggcgtgc agcagagccc ctgcaacgcc ctgtgcgtgg cccacatcgg ccccgtggat     780
agcggcaacc acaacctgat caccaacaac cacgaccagc accagcgccg caacaacagc     840
```

-continued

```
aacagcagcg ccactcccat cgtgcagttc cagggcgaga gcaactgcct gaagtgcttc      900
cgctaccgcc tgaacgatcg ccaccgccac ctgttcgacc tgatcagcag cacctggcac      960
tgggccagca gcaaggctcc ccacaagcac gccatcgtga ccgtgaccta cgacagcgag     1020
gagcagcgcc agcagttcct ggacgtggtg aagatccctc ccaccatcag ccacaagctg     1080
ggcttcatga gcctgcacct gctgtaa                                          1107
```

<210> SEQ ID NO 8
<211> LENGTH: 1098
<212> TYPE: DNA
<213> ORGANISM: Artificial Sequence
<220> FEATURE:
<223> OTHER INFORMATION: Codon-Optimized HPV18 E2

<400> SEQUENCE: 8

```
atgcagactc ccaaggagac cctgagcgag cgcctgagcg ccctgcagga caagatcatc       60
gaccactacg agaacgacag caaggacatc gacagccaga tccagtactg cagctgatc      120 cgctgggaga cgccatctt cttcgccgct cgcgagcacg ggatccagac cctgaaccac       180
caggtggtgc ccgcctacaa catcagcaag agcaaggccc acaaggccat cgagctgcag      240
atggccctgc agggcctggc ccagagcgcc tacaagaccg aggactggac cctgcaggac      300
acctgcgagg agctgtggaa caccgagccc acccactgct tcaagaaggg aggccagacc      360
gtgcaggtgt acttcgacgg caacaaggac aactgcatga actacgtggc ctgggacagc      420
gtgtactaca tgaccgacgc cggcacctgg acaagaccg ccacctgcgt gagccaccgc      480
ggcctgtact acgtgaagga gggctacaac accttctaca tcgagttcaa gagcgagtgc      540
gagaagtacg gcaacaccgg cacctgggag gtgcacttcg gcaacaacgt gatcgactgc      600
aacgacagca tgtgcagcac cagcgacgac accgtgagcg ccacccagct ggtgaagcag      660
ctgcagcaca ctcccagccc ctacagcagc ccgtgagcg tgggcaccgc caagacctac      720
ggccagacca gcgccgccac tcgccctggc cactgcggcc tggccgagaa gcagcactgc      780
gggcccgtga accctctgct gggcgccgcc accgccaccg caacaacaa gcgccgcaag      840 ctgtgcagcg gcaacaccac tcccatcatc cacctgaagg gcgaccgcaa cagcctgaag      900
tgcctgcggt accgcctgcg caagcacagc gaccactacc gcgacatcag cagcacctgg      960
cactggaccg gcgccgggaa cgagaagacc ggcatcctga ccgtgaccta ccacagcgag     1020
acccagcgca ccaagttcct gaacaccgtg gccatccccg acagcgtgca gatcctggtg     1080
ggctacatga ccatgtaa                                                   1098
```

<210> SEQ ID NO 9
<211> LENGTH: 129
<212> TYPE: DNA
<213> ORGANISM: Artificial Sequence
<220> FEATURE:
<223> OTHER INFORMATION: Codon-Optimized HPV16 L1 fragment

<400> SEQUENCE: 9

```
atgagcctgt ggctgcccag cgaggccacc gtgtacctgc ctcccgtgcc cgtgagcaag       60
gtggtgagca ccgacgagta cgtggcccgc accaacatct actaccacgc cggcaccagc      120
cgcctgctg                                                              129
```

<210> SEQ ID NO 10
<211> LENGTH: 129
<212> TYPE: DNA
<213> ORGANISM: Artificial Sequence

```
<220> FEATURE:
<223> OTHER INFORMATION: Codon-Optimized HPV16 L1 fragment

<400> SEQUENCE: 10
cgcatccacc tgcccgaccc caacaagttc ggcttccccg acacaagctt ctacaacccc      60
gacacccagc gcctggtgtg ggcctgcgtg ggcgtggagg tgggccgcgg ccagcccctg     120
ggcgtgggc                                                             129

<210> SEQ ID NO 11
<211> LENGTH: 129
<212> TYPE: DNA
<213> ORGANISM: Artificial Sequence
<220> FEATURE:
<223> OTHER INFORMATION: Codon-Optimized HPV16 L1 fragment

<400> SEQUENCE: 11
gagtgcatca gcatggacta caagcagacc cagctgtgcc tgatcggctg caagcctccc      60
atcggcgagc actggggcaa gggcagcccc tgcaccaacg tggccgtgaa ccccggcgac     120
tgccctccc                                                             129

<210> SEQ ID NO 12
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 12
gccaacaaga gcgaggtgcc cctggacatc tgcaccagca tctgcaagta ccccgactac      60
atcaagatgg tgagcgagcc ctacggcgac agcctgttct ctacctgcg ccgcgagcag     120 atgttcgtgc gc                                                         132

<210> SEQ ID NO 13
<211> LENGTH: 129
<212> TYPE: DNA
<213> ORGANISM: Artificial Sequence
<220> FEATURE:
<223> OTHER INFORMATION: Codon-Optimized HPV16 L1 fragment

<400> SEQUENCE: 13
gccagcagca actacttccc cactcccagc ggcagcatgg tgaccagcga cgcccaaatc      60
ttcaacaagc cctactggct gcagcgcgcc cagggccaca caacggcat ctgctggggc     120 aaccagctg                                                             129

<210> SEQ ID NO 14
<211> LENGTH: 135
<212> TYPE: DNA
<213> ORGANISM: Artificial Sequence
<220> FEATURE:
<223> OTHER INFORMATION: Codon-Optimized HPV16 L1 fragment

<400> SEQUENCE: 14
gagtacctgc gccacggcga ggagtacgac ctgcagttca tcttccagct gtgcaagatc      60
accctgaccg ccgacgtgat gacctacatc cacagcatga acagcaccat cctggaggac     120
tggaacttcg gcctg                                                      135

<210> SEQ ID NO 15
<211> LENGTH: 135
<212> TYPE: DNA
```

<213> ORGANISM: Artificial Sequence
<220> FEATURE:
<223> OTHER INFORMATION: Codon-Optimized HPV16 L1 fragment

<400> SEQUENCE: 15
gctcccaagg aggatcccct gaagaagtac accttctggg aggtgaacct gaaggagaag    60
ttcagcgccg acctggacca gttccccctg ggccgcaagt tcctgctgca ggccggcctg   120
aaggccaagc ccaag                                                   135

<210> SEQ ID NO 16
<211> LENGTH: 135
<212> TYPE: DNA
<213> ORGANISM: Artificial Sequence
<220> FEATURE:
<223> OTHER INFORMATION: Codon-Optimized HPV16 L1 fragment

<400> SEQUENCE: 16
gttggggtcg gcaggtgga tgcggaacac gcggtactgc aggccgctca ccttgggcac    60
caggatcttg ttgttgttgg gcttcttgat ggggaagtag gggtggccca cggccagcag   120
gcggctggtg ccggc                                                   135

<210> SEQ ID NO 17
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 17
cttgtagtcc atgctgatgc actcgcggtt gtccacgccg gcgttggcgg cgtaggcgct    60
ggcgttctcg gtgtcgtcca gcttgttcag caggggtgg ccgctgatgc ccacgcccag   120
gggctggccg cg                                                      132

<210> SEQ ID NO 18
<211> LENGTH: 129
<212> TYPE: DNA
<213> ORGANISM: Artificial Sequence
<220> FEATURE:
<223> OTHER INFORMATION: Codon-Optimized HPV16 L1 fragment

<400> SEQUENCE: 18
caggggcacc tcgctcttgt tggcctgcag ggtggtgaag tccatggcgc cgaagccggt    60
gtccaccatg tcgccgtcct ggatcacggt gttgatcagc tccaggggag ggcagtcgcc   120
ggggttcac                                                          129

<210> SEQ ID NO 19
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 19
gggagtgggg aagtagttgc tgctggccag gttggcggtg ctgccgctgc ccttgatgta    60
caggtcgtcg ggcacgttct cgcccacggc gccggcgcgg ttgaacaggt ggcgcacgaa   120
catctgctcg cg                                                      132

<210> SEQ ID NO 20
<211> LENGTH: 144

<212> TYPE: DNA
<213> ORGANISM: Artificial Sequence
<220> FEATURE:
<223> OTHER INFORMATION: Codon-Optimized HPV16 L1 fragment

<400> SEQUENCE: 20

```
ctcctcgccg tggcgcaggt actccttgaa gttggtgttc ttgtaggtgg tctcgctggt      60
gctgatggcg gcgcacaggc tcatgttggt gctgcgggtg gtgtccacca cggtcacgaa     120
cagctggttg ccccagcaga tgcc                                            144
```

<210> SEQ ID NO 21
<211> LENGTH: 132
<212> TYPE: DNA
<213> ORGANISM: Artificial Sequence
<220> FEATURE:
<223> OTHER INFORMATION: Codon-Optimized HPV16 L1 fragment

<400> SEQUENCE: 21

```
cttcagggga tcctccttgg gagcgggagg ggtgtgcttc tggcaggcga tggcctggct      60
ggtcacgaag cggtaggtgt cctccagggt accgccggga gggggctgca ggccgaagtt    120
ccagtcctcc ag                                                         132
```

<210> SEQ ID NO 22
<211> LENGTH: 123
<212> TYPE: DNA
<213> ORGANISM: Artificial Sequence
<220> FEATURE:
<223> OTHER INFORMATION: Codon-Optimized HPV16 L1 fragment

<400> SEQUENCE: 22

```
cactagagat ctgaattctt acagcttgcg cttcttgcgc ttggcggtgg tgctggtgct      60
gctggtggtg ggggtggcct tgcgcttgcc cagggtgaac ttgggcttgg ccttcaggcc    120
ggc                                                                   123
```

<210> SEQ ID NO 23
<211> LENGTH: 21
<212> TYPE: DNA
<213> ORGANISM: Artificial Sequence
<220> FEATURE:
<223> OTHER INFORMATION: Codon-Optimized HPV16 L1 fragment

<400> SEQUENCE: 23

```
cgcggccagc ccctgggcgt g                                                21
```

<210> SEQ ID NO 24
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 24

```
gcccacgccc aggggctggc cgcg                                             24
```

<210> SEQ ID NO 25
<211> LENGTH: 21
<212> TYPE: DNA
<213> ORGANISM: Artificial Sequence
<220> FEATURE:
<223> OTHER INFORMATION: Codon-Optimized HPV16 L1 fragment

<400> SEQUENCE: 25

```
gccaacaaga gcgaggtgcc c                                                       21

<210> SEQ ID NO 26
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 26 cagggggcacc tcgctcttgt tggc                                                   24

<210> SEQ ID NO 27
<211> LENGTH: 23
<212> TYPE: DNA
<213> ORGANISM: Artificial Sequence
<220> FEATURE:
<223> OTHER INFORMATION: Codon-Optimized HPV16 L1 fragment

<400> SEQUENCE: 27
gccagcagca actacttccc cac                                                     23

<210> SEQ ID NO 28
<211> LENGTH: 23
<212> TYPE: DNA
<213> ORGANISM: Artificial Sequence
<220> FEATURE:
<223> OTHER INFORMATION: Codon-Optimized HPV16 L1 fragment

<400> SEQUENCE: 28
gggagtgggg aagtagttgc tgc                                                     23

<210> SEQ ID NO 29
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 29
ctggaggact ggaacttcgg cctg                                                    24

<210> SEQ ID NO 30
<211> LENGTH: 24
<212> TYPE: DNA
<213> ORGANISM: Artificial Sequence
<220> FEATURE:
<223> OTHER INFORMATION: Codon-Optimized HPV16 L1 fragment

<400> SEQUENCE: 30
caggccgaag ttccagtcct ccag                                                    24

<210> SEQ ID NO 31
<211> LENGTH: 25
<212> TYPE: DNA
<213> ORGANISM: Artificial Sequence
<220> FEATURE:
<223> OTHER INFORMATION: Codon-Optimized HPV16 L1 fragment

<400> SEQUENCE: 31
cactagagat ctgaattctt acagc                                                   25

<210> SEQ ID NO 32
<211> LENGTH: 38
<212> TYPE: DNA
<213> ORGANISM: Artificial Sequence
```

-continued

<220> FEATURE:
<223> OTHER INFORMATION: Codon-Optimized HPV16 L1 fragment

<400> SEQUENCE: 32
catctcagat ctgccaccat gagcctgtgg ctgcccag         38

<210> SEQ ID NO 33
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 33
atggccgacc ccgccggcac caacggcgag gagggcaccg gctgcaacgg ctggttctac      60
gtggaggccg tggtggagaa gaagaccggc gacgccatca gcgacgacga gaacgagaac     120
gacagcgac                                                             129

<210> SEQ ID NO 34
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 34
gtgctgcttg gcctcctggg cgtgaacag ggcgtgggcg gtctcggtct cggcctgggt       60
caggtagtcg ttgtcgttca cgatgaagtc caccaggtcc tcgccggtgt cgctgtcgtt    120
ctcgttctcg tc                                                         132

<210> SEQ ID NO 35
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 35
gcccaggagg ccaagcagca ccgcgacgcc gtgcaggtgc tgaagcgcaa gtacctgggc      60
agccccctga gcgacatcag cggctgcgtc gacaacaaca tcagcccccg cctgaaggcc    120
atctgcatcg ag                                                         132

<210> SEQ ID NO 36
<211> LENGTH: 131
<212> TYPE: DNA
<213> ORGANISM: Artificial Sequence
<220> FEATURE:
<223> OTHER INFORMATION: Codon-Optimized HPV16 E1 fragment

<400> SEQUENCE: 36
ctcgtggcgg ccctccacct gcagcatctg ctgggtctcc acctcggtgt tgccgtagcc      60
gctgtcctcg ctctcgaaca ggcggcgctt ggcggcgcgg ctctgcttct cgatgcagat    120
ggccttcagg c                                                          131

<210> SEQ ID NO 37
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 37
caggtggagg gccgccacga gaccgagacc ccctgcagcc agtacagcgg cggcagcggc    60
ggcggctgca gccagtacag cagcggcagc ggcggcgagg cgtgagcga cgccacacc    120 atctgccaga cc    132

<210> SEQ ID NO 38
<211> LENGTH: 135
<212> TYPE: DNA
<213> ORGANISM: Artificial Sequence
<220> FEATURE:
<223> OTHER INFORMATION: Codon-Optimized HPV16 E1 fragment

<400> SEQUENCE: 38
cttgaagggg cgcaccagct cgctgaagct cacgccgtac agctccttga acttggccag    60
catggcggcc ttggcgttgc tggtcttcag cacgttcagg atgttggtca gagggtctg    120 gcagatggtg tggcg    135

<210> SEQ ID NO 39
<211> LENGTH: 135
<212> TYPE: DNA
<213> ORGANISM: Artificial Sequence
<220> FEATURE:
<223> OTHER INFORMATION: Codon-Optimized HPV16 E1 fragment

<400> SEQUENCE: 39
gagctggtgc gccccttcaa gagcaacaag agcacctgct cgactggtg catcgccgcc     60 ttcggcctga cccccagcat cgccgacagc atcaagaccc tgctgcagca gtactgcctg    120
tacctgcaca tccag    135

<210> SEQ ID NO 40
<211> LENGTH: 136
<212> TYPE: DNA
<213> ORGANISM: Artificial Sequence
<220> FEATURE:
<223> OTHER INFORMATION: Codon-Optimized HPV16 E1 fragment

<400> SEQUENCE: 40 catgggctc acgcacagca gcttgctcag cagcttctcg atggtctcgc ggttcttgcc     60
gcacttgtag cgcaccagca gcagcaccac catgccccag ctgcaggcca ggctctggat    120
gtgcaggtac aggcag    136

<210> SEQ ID NO 41
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 41
ctgctgtgcg tgagccccat gtgcatgatg atcgagcctc ccaagcttcg cagcaccgcc    60
gccgccctgt actggtacaa gaccggcatc agcaacatca gcgaggtgta cggcgacacc    120
cccgagtgga tc    132

<210> SEQ ID NO 42
<211> LENGTH: 129
<212> TYPE: DNA
<213> ORGANISM: Artificial Sequence
<220> FEATURE:
<223> OTHER INFORMATION: Codon-Optimized HPV16 E1 fragment

```
<400> SEQUENCE: 42
ggcgatctcg ctgtcgtcca cgatgtcgtt gtcgtaggcc cactgcacca tctggctcag      60
ctcgaaggtg cagtcgttga agctgtgctg cagcacggtc tggcgctgga tccactcggg     120
ggtgtcgcc                                                             129

<210> SEQ ID NO 43
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 43
gtggacgaca gcgagatcgc ctacaagtac gcccagctgg ccgacaccaa cagcaacgcc      60
agcgccttcc tgaagagcaa cagccaggcc aagatcgtga aggactgcgc caccatgtgc     120
cgccactac                                                             129

<210> SEQ ID NO 44
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 44
gtagcgcagg aacatcacga tctgcttgcg gtcgccgccg tcgtccacgc ggtcgcagcg      60
gtacttgatc cactggctca tgctcatctg cttcttctcg gcgcgcttgt agtggcggca     120
catggtggc                                                             129

<210> SEQ ID NO 45
<211> LENGTH: 129
<212> TYPE: DNA
<213> ORGANISM: Artificial Sequence
<220> FEATURE:
<223> OTHER INFORMATION: Codon-Optimized HPV16 E1 fragment

<400> SEQUENCE: 45
cagatcgtga tgttcctgcg ctaccagggc gtggaattca tgagcttcct gaccgccctg      60
aagcgcttcc tgcagggcat ccccaagaag aactgcatcc tgctgtacgg cgccgccaac     120
accgacaag                                                             129

<210> SEQ ID NO 46
<211> LENGTH: 130
<212> TYPE: DNA
<213> ORGANISM: Artificial Sequence
<220> FEATURE:
<223> OTHER INFORMATION: Codon-Optimized HPV16 E1 fragment

<400> SEQUENCE: 46
gccgatcttg gcgtcggcca ggggctgcag ccagaagtgg ctcttgctgt tcacgaagca      60
gatcacgctg ccctgcagga acttcatcag gctcatgccg acaggctct tgtcggtgtt     120 ggcggcgccg                                                            130

<210> SEQ ID NO 47
<211> LENGTH: 129
<212> TYPE: DNA
<213> ORGANISM: Artificial Sequence
<220> FEATURE:
```

<223> OTHER INFORMATION: Codon-Optimized HPV16 E1 fragment

<400> SEQUENCE: 47

```
ctggccgacg ccaagatcgg catgctggac gacgccaccg tgccctgctg gaactacatc        60
gacgacaacc tgcgcaacgc cctggacggc aacctggtga gcatggacgt gaagcaccgc       120
cccctggtg                                                               129
```

<210> SEQ ID NO 48
<211> LENGTH: 132
<212> TYPE: DNA
<213> ORGANISM: Artificial Sequence
<220> FEATURE:
<223> OTHER INFORMATION: Codon-Optimized HPV16 E1 fragment

<400> SEQUENCE: 48

```
gaactcgttg gggaaggtga acaccaccag gcggttgtgc aggtagggcc agcggctgtc        60
ggtgccggcg ttgatgttgc tggtgatcag caggggaggg cacttcagct gcaccagggg       120
gcggtgcttc ac                                                           132
```

<210> SEQ ID NO 49
<211> LENGTH: 126
<212> TYPE: DNA
<213> ORGANISM: Artificial Sequence
<220> FEATURE:
<223> OTHER INFORMATION: Codon-Optimized HPV16 E1 fragment

<400> SEQUENCE: 49

```
gtgttcacct tccccaacga gttccccttc gacgagaacg taaccccgt gtacgagctg         60
aacgacaaga actggaagag cttcttcagc cgcacctgga gccgcctgag cctgcacgag       120
gacgag                                                                  126
```

<210> SEQ ID NO 50
<211> LENGTH: 105
<212> TYPE: DNA
<213> ORGANISM: Artificial Sequence
<220> FEATURE:
<223> OTHER INFORMATION: Codon-Optimized HPV16 E1 fragment

<400> SEQUENCE: 50

```
catgagagat ctttacaggg tgttggtgtt ctggccgctc acgcacttga aggtgggcag        60
gctgtcgccg tcgttctcct tgtcctcgtc ctcgtgcagg ctcag                       105
```

<210> SEQ ID NO 51
<211> LENGTH: 23
<212> TYPE: DNA
<213> ORGANISM: Artificial Sequence
<220> FEATURE:
<223> OTHER INFORMATION: Codon-Optimized HPV16 E1 fragment

<400> SEQUENCE: 51

```
gcctgaaggc catctgcatc gag                                                23
```

<210> SEQ ID NO 52
<211> LENGTH: 23
<212> TYPE: DNA
<213> ORGANISM: Artificial Sequence
<220> FEATURE:
<223> OTHER INFORMATION: Codon-Optimized HPV16 E1 fragment

<400> SEQUENCE: 52

```
ctcgatgcag atggccttca ggc                                                23
```

<210> SEQ ID NO 53
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 53
gagctggtgc gccccttcaa g                                              21

<210> SEQ ID NO 54
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 54
cttgaagggg cgcaccagct c                                              21

<210> SEQ ID NO 55
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 55
ctgctgtgcg tgagccccat g                                              21

<210> SEQ ID NO 56
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 56 catgggctc acgcacagca g                                               21

<210> SEQ ID NO 57
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 57
gccaccatgt gccgccacta c                                              21

<210> SEQ ID NO 58
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 58
gtagtggcgg cacatggtgg c                                              21

<210> SEQ ID NO 59
<211> LENGTH: 21
<212> TYPE: DNA
<213> ORGANISM: Artificial Sequence
<220> FEATURE:

<223> OTHER INFORMATION: Codon-Optimized HPV16 E1 fragment

<400> SEQUENCE: 59
ctggccgacg ccaagatcgg c                                          21

<210> SEQ ID NO 60
<211> LENGTH: 21
<212> TYPE: DNA
<213> ORGANISM: Artificial Sequence
<220> FEATURE:
<223> OTHER INFORMATION: Codon-Optimized HPV16 E1 fragment

<400> SEQUENCE: 60
gccgatcttg gcgtcggcca g                                          21

<210> SEQ ID NO 61
<211> LENGTH: 24
<212> TYPE: DNA
<213> ORGANISM: Artificial Sequence
<220> FEATURE:
<223> OTHER INFORMATION: Codon-Optimized HPV16 E1 fragment

<400> SEQUENCE: 61
gtgttcacct tccccaacga gttc                                       24

<210> SEQ ID NO 62
<211> LENGTH: 24
<212> TYPE: DNA
<213> ORGANISM: Artificial Sequence
<220> FEATURE:
<223> OTHER INFORMATION: Codon-Optimized HPV16 E1 fragment

<400> SEQUENCE: 62
gaactcgttg gggaaggtga acac                                       24

<210> SEQ ID NO 63
<211> LENGTH: 25
<212> TYPE: DNA
<213> ORGANISM: Artificial Sequence
<220> FEATURE:
<223> OTHER INFORMATION: Codon-Optimized HPV16 E1 fragment

<400> SEQUENCE: 63
catgagagat ctttacaggg tgttg                                      25

<210> SEQ ID NO 64
<211> LENGTH: 38
<212> TYPE: DNA
<213> ORGANISM: Artificial Sequence
<220> FEATURE:
<223> OTHER INFORMATION: Codon-Optimized HPV16 E1 fragment

<400> SEQUENCE: 64
catctcagat ctgccaccat ggccgacccc gccggcac                        38

<210> SEQ ID NO 65
<211> LENGTH: 99
<212> TYPE: DNA
<213> ORGANISM: Artificial Sequence
<220> FEATURE:
<223> OTHER INFORMATION: Codon-Optimized HPV16 E2 fragment

<400> SEQUENCE: 65
atggagaccc tgtgccagcg cctgaacgtg tgccaggaca agatcctgac ccactacgag    60
aacgacagca ccgacctgcg cgaccacatc gactactgg                           99

<210> SEQ ID NO 66
<211> LENGTH: 104
<212> TYPE: DNA
<213> ORGANISM: Artificial Sequence
<220> FEATURE:
<223> OTHER INFORMATION: Codon-Optimized HPV16 E2 fragment

<400> SEQUENCE: 66
ccaccaggtg gtgcccaccc tggccgtgag caagaacaag gccctgcagg ccgccgagct    60
gcagctgacc ctggagacga tctacaacag ccagtacagc aacg                   104

<210> SEQ ID NO 67
<211> LENGTH: 108
<212> TYPE: DNA
<213> ORGANISM: Artificial Sequence
<220> FEATURE:
<223> OTHER INFORMATION: Codon-Optimized HPV16 E2 fragment

<400> SEQUENCE: 67
ccggctgcat caagaagcac ggctacaccg tggaggtgca gttcgacggc gacatctgca    60
acaccatgca ctacaccaac tggacccaca tttacatctg tgaggagg               108

<210> SEQ ID NO 68
<211> LENGTH: 104
<212> TYPE: DNA
<213> ORGANISM: Artificial Sequence
<220> FEATURE:
<223> OTHER INFORMATION: Codon-Optimized HPV16 E2 fragment

<400> SEQUENCE: 68
cgtgcacgag gggatccgca cctacttcgt gcagttcaag gacgacgccg agaagtacag    60
caagaacaag gtgtgggagg tgcacgccgg aggccaggtg atcc                   104

<210> SEQ ID NO 69
<211> LENGTH: 110
<212> TYPE: DNA
<213> ORGANISM: Artificial Sequence
<220> FEATURE:
<223> OTHER INFORMATION: Codon-Optimized HPV16 E2 fragment

<400> SEQUENCE: 69
ggccaaccac agcgccgcca cccacaccaa ggccgtggcc ctgggcaccg aggagaccca    60
gaccacaatc cagcgccctc gcagcgagcc cgacaccggc aaccnctgcc             110

<210> SEQ ID NO 70
<211> LENGTH: 107
<212> TYPE: DNA
<213> ORGANISM: Artificial Sequence
<220> FEATURE:
<223> OTHER INFORMATION: Codon-Optimized HPV16 E2 fragment

<400> SEQUENCE: 70
gccacaaggg ccggatcaac tgcaacagca acaccacccc tatcgtgcac ctgaagggcg    60
acgccaacac cctgaagtgc ctgcggtacc gcttcaagaa gcactgc                107

<210> SEQ ID NO 71
<211> LENGTH: 113
<212> TYPE: DNA
<213> ORGANISM: Artificial Sequence
<220> FEATURE:
<223> OTHER INFORMATION: Codon-Optimized HPV16 E2 fragment -continued

<400> SEQUENCE: 71
ccagggtggg caccacctgg tggttgatgt gcttgaagcc catctcgcgg gccttgtagt        60
agatggcgca ggccaggcgc atgtgcttcc agtagtcgat gtggtcgcgc agg              113

<210> SEQ ID NO 72
<211> LENGTH: 101
<212> TYPE: DNA
<213> ORGANISM: Artificial Sequence
<220> FEATURE:
<223> OTHER INFORMATION: Codon-Optimized HPV16 E2 fragment

<400> SEQUENCE: 72
gccgtgcttc ttgatgcagc cggtaggggc ggtcaggtac acctccaggc tcacgtcctg        60
cagggtccac ttctcgttgc tgtactggct gttgtagatc g                           101

<210> SEQ ID NO 73
<211> LENGTH: 98
<212> TYPE: DNA
<213> ORGANISM: Artificial Sequence
<220> FEATURE:
<223> OTHER INFORMATION: Codon-Optimized HPV16 E2 fragment

<400> SEQUENCE: 73
ggtgcggatc ccctcgtgca cgtagtacag gccgtagtag tccacctggc cctccaccac        60
ggtcacgctg gcctcctcac agatgtaaat gtgggtcc                               98

<210> SEQ ID NO 74
<211> LENGTH: 110
<212> TYPE: DNA
<213> ORGANISM: Artificial Sequence
<220> FEATURE:
<223> OTHER INFORMATION: Codon-Optimized HPV16 E2 fragment

<400> SEQUENCE: 74
gggtggcggc gctgtggttg ccaggtgct ggcggatcgt ctcggggctg ctcacctcgt         60
tgctgctgaa cacgctggtg gggcacagga tcacctggcc tccggcgtgc                  110

<210> SEQ ID NO 75
<211> LENGTH: 111
<212> TYPE: DNA
<213> ORGANISM: Artificial Sequence
<220> FEATURE:
<223> OTHER INFORMATION: Codon-Optimized HPV16 E2 fragment

<400> SEQUENCE: 75
gcagttgatc cggcccttgt ggctgctgtt gaaggcggtc aggatagggg cgctgtcgac        60
gctgtcgcgg tgcagcagct tggtggtgtg gcaggggttg ccggtgtcgg g                111

<210> SEQ ID NO 76
<211> LENGTH: 110
<212> TYPE: DNA
<213> ORGANISM: Artificial Sequence
<220> FEATURE:
<223> OTHER INFORMATION: Codon-Optimized HPV16 E2 fragment

<400> SEQUENCE: 76
cgtaggtcag ggtcacgata gcgctcttgt gcttcacgtt gtggccggtc cagtgccagg        60
tgctgctcac ggcggtgtac agcttgcagt gcttcttgaa gcggtaccgc                  110

<210> SEQ ID NO 77
<211> LENGTH: 111

<210> SEQ ID NO 77
<211> LENGTH: 111
<212> TYPE: DNA
<213> ORGANISM: Artificial Sequence
<220> FEATURE:
<223> OTHER INFORMATION: Codon-Optimized HPV16 E2 fragment

<400> SEQUENCE: 77
tttagatgct catgaagccg gtgctcacgg tgatggtctt ggggatcttc acctggctca      60
ggaactggtc gcgctgccac tcgctgtcgt aggtcagggt cacgatagcg c              111

<210> SEQ ID NO 78
<211> LENGTH: 50
<212> TYPE: DNA
<213> ORGANISM: Artificial Sequence
<220> FEATURE:
<223> OTHER INFORMATION: Codon-Optimized HPV16 E2 fragment

<400> SEQUENCE: 78
cgagctgata tcgaattcag atctgccacc atggagaccc tgtgccagcg                 50

<210> SEQ ID NO 79
<211> LENGTH: 45
<212> TYPE: DNA
<213> ORGANISM: Artificial Sequence
<220> FEATURE:
<223> OTHER INFORMATION: Codon-Optimized HPV16 E2 fragment

<400> SEQUENCE: 79
ggttgcagat ctagactcga gtttagatgc tcatgaagcc ggtgc                      45

<210> SEQ ID NO 80
<211> LENGTH: 21
<212> TYPE: DNA
<213> ORGANISM: Artificial Sequence
<220> FEATURE:
<223> OTHER INFORMATION: Codon-Optimized HPV16 E2 fragment

<400> SEQUENCE: 80
ccggctgcat caagaagcac g                                                21

<210> SEQ ID NO 81
<211> LENGTH: 19
<212> TYPE: DNA
<213> ORGANISM: Artificial Sequence
<220> FEATURE:
<223> OTHER INFORMATION: Codon-Optimized HPV16 E2 fragment

<400> SEQUENCE: 81
ggccaaccac agcgccgcc                                                   19

<210> SEQ ID NO 82
<211> LENGTH: 21
<212> TYPE: DNA
<213> ORGANISM: Artificial Sequence
<220> FEATURE:
<223> OTHER INFORMATION: Codon-Optimized HPV16 E2 fragment

<400> SEQUENCE: 82
gccgtgcttc ttgatgcagc c                                                21

<210> SEQ ID NO 83
<211> LENGTH: 17
<212> TYPE: DNA
<213> ORGANISM: Artificial Sequence
<220> FEATURE:
<223> OTHER INFORMATION: Codon-Optimized HPV16 E2 fragment

```
<400> SEQUENCE: 83
gggtggcggc gctgtgg                                                    17

<210> SEQ ID NO 84
<211> LENGTH: 22
<212> TYPE: DNA
<213> ORGANISM: Artificial Sequence
<220> FEATURE:
<223> OTHER INFORMATION: Codon-Optimized HPV16 E2 fragment

<400> SEQUENCE: 84
cgtaggtcag ggtcacgata gc                                              22

<210> SEQ ID NO 85
<211> LENGTH: 109
<212> TYPE: DNA
<213> ORGANISM: Artificial Sequence
<220> FEATURE:
<223> OTHER INFORMATION: Codon-Optimized HPV16 E7 fragment

<400> SEQUENCE: 85
ggccggagat ctgatatcga attcgccacc atgcacggcg acacccccac cctgcacgag      60
tacatgctgg acctgcagcc cgagaccacc gacctgtacg gctacggcc               109

<210> SEQ ID NO 86
<211> LENGTH: 106
<212> TYPE: DNA
<213> ORGANISM: Artificial Sequence
<220> FEATURE:
<223> OTHER INFORMATION: Codon-Optimized HPV16 E7 fragment

<400> SEQUENCE: 86
gccgagcccg accgcgccca ctacaacatc gtgaccttct gctgcaagtg cgacagcacc      60
ctgcgcctgt gcgtgcagag cacccacgtc gacatccgca ccctgg                  106

<210> SEQ ID NO 87
<211> LENGTH: 96
<212> TYPE: DNA
<213> ORGANISM: Artificial Sequence
<220> FEATURE:
<223> OTHER INFORMATION: Codon-Optimized HPV16 E7 fragment

<400> SEQUENCE: 87
gggcgcggtc gggctcggcc tggccggcgg ggccgtcgat ctcgtcctct tcctcgctgc      60
tgtcgttcag ctggccgtag ccgtacaggt cggtgg                              96

<210> SEQ ID NO 88
<211> LENGTH: 106
<212> TYPE: DNA
<213> ORGANISM: Artificial Sequence
<220> FEATURE:
<223> OTHER INFORMATION: Codon-Optimized HPV16 E7 fragment

<400> SEQUENCE: 88
ccgcggcaga tctagactcg agtttagggc ttctggctgc agattgggca cacgattccc      60
agggtgccca tcagcaggtc ctccagggtg cggatgtcga cgtggg                  106

<210> SEQ ID NO 89
<211> LENGTH: 25
<212> TYPE: DNA
<213> ORGANISM: Artificial Sequence
<220> FEATURE:
<223> OTHER INFORMATION: Codon-Optimized HPV16 E7 fragment
```

<400> SEQUENCE: 89
ggccggagat ctgatatcga attcg                                              25

<210> SEQ ID NO 90
<211> LENGTH: 20
<212> TYPE: DNA
<213> ORGANISM: Artificial Sequence
<220> FEATURE:
<223> OTHER INFORMATION: Codon-Optimized HPV16 E7 fragment

<400> SEQUENCE: 90
ccgcggcaga tctagactcg                                                    20

<210> SEQ ID NO 91
<211> LENGTH: 105
<212> TYPE: DNA
<213> ORGANISM: Artificial Sequence
<220> FEATURE:
<223> OTHER INFORMATION: Codon-Optimized HPV6a E7 fragment

<400> SEQUENCE: 91
gtcacagatc tgatatcgaa ttccaccatg cacggccgcc acgtgaccct gaaggacatc        60
gtgctggacc tgcagcctcc cgaccccgtg ggcctgcact gctac                       105

<210> SEQ ID NO 92
<211> LENGTH: 105
<212> TYPE: DNA
<213> ORGANISM: Artificial Sequence
<220> FEATURE:
<223> OTHER INFORMATION: Codon-Optimized HPV6a E7 fragment

<400> SEQUENCE: 92
ctggaagtgc tgcttcaggg gctggctgtc ctggccgtcc acctcgtcca cctcgtcctc        60
gctgctgtcc accagctgct cgtagcagtg caggcccacg ggtc                        105

<210> SEQ ID NO 93
<211> LENGTH: 107
<212> TYPE: DNA
<213> ORGANISM: Artificial Sequence
<220> FEATURE:
<223> OTHER INFORMATION: Codon-Optimized HPV6a E7 fragment

<400> SEQUENCE: 93
ccagcccctg aagcagcact tccagatcgt gacctgctgc tgcggctgcg acagcaacgt        60
gcgcctggtg gtgcagtgca ccgagaccga catccgcgag gtgcagc                    107

<210> SEQ ID NO 94
<211> LENGTH: 102
<212> TYPE: DNA
<213> ORGANISM: Artificial Sequence
<220> FEATURE:
<223> OTHER INFORMATION: Codon-Optimized HPV6a E7 fragment

<400> SEQUENCE: 94
cagtcagatc tagagatatc tttaggtctt gggagcgcag atggggcaca cgatgttcag        60
ggtacccagc aggagctgct gcacctcgcg gatgtcggtc tc                          102

<210> SEQ ID NO 95
<211> LENGTH: 24
<212> TYPE: DNA
<213> ORGANISM: Artificial Sequence
<220> FEATURE:

<223> OTHER INFORMATION: PCR Primer

<400> SEQUENCE: 95
gtcacagatc tgatatcgaa ttcc                                            24

<210> SEQ ID NO 96
<211> LENGTH: 26
<212> TYPE: DNA
<213> ORGANISM: Artificial Sequence
<220> FEATURE:
<223> OTHER INFORMATION: PCR Primer

<400> SEQUENCE: 96
cagtcagatc tagagatatc tttagg                                          26

<210> SEQ ID NO 97
<211> LENGTH: 109
<212> TYPE: DNA
<213> ORGANISM: Artificial Sequence
<220> FEATURE:
<223> OTHER INFORMATION: Codon-Optimized HPV18 E7 fragment

<400> SEQUENCE: 97
gtcacagatc tgatatcgaa ttccaccatg cacggcccca aggccaccct gcaggacatc     60
gtgctgcacc tggagcccca gaacgagatc cccgtggacc tgctgtgcc                109

<210> SEQ ID NO 98
<211> LENGTH: 111
<212> TYPE: DNA
<213> ORGANISM: Artificial Sequence
<220> FEATURE:
<223> OTHER INFORMATION: Codon-Optimized HPV18 E7 fragment

<400> SEQUENCE: 98
gggctcggcc ctgcgagcgg gcaggtgctg gtggttcacg ccgtcgatct cgtcgttctc     60
ctcctcgctg tcgctcagct gctcgtggca cagcaggtcc acggggatct c             111

<210> SEQ ID NO 99
<211> LENGTH: 108
<212> TYPE: DNA
<213> ORGANISM: Artificial Sequence
<220> FEATURE:
<223> OTHER INFORMATION: Codon-Optimized HPV18 E7 fragment

<400> SEQUENCE: 99
gcccgctcgc agggccgagc cccagcgcca caccatgctg tgcatgtgct gcaagtgcga     60
ggcccgcatc gagctggtgg tggagagcag cgctgacgac ctgcgcgc                 108

<210> SEQ ID NO 100
<211> LENGTH: 109
<212> TYPE: DNA
<213> ORGANISM: Artificial Sequence
<220> FEATURE:
<223> OTHER INFORMATION: Codon-Optimized HPV18 E7 fragment

<400> SEQUENCE: 100
cagtcagatc tagagatatc tttactgctg gctggcgcac caggggcaca cgaagctcag     60
ggtgttcagg aacagctgct ggaaggcgcg caggtcgtca gcgctgctc               109

<210> SEQ ID NO 101
<211> LENGTH: 26
<212> TYPE: DNA
<213> ORGANISM: Artificial Sequence

```
-continued

<220> FEATURE:
<223> OTHER INFORMATION: PCR Fragment

<400> SEQUENCE: 101
gtcacagatc tgatatcgaa ttccac                                          26

<210> SEQ ID NO 102
<211> LENGTH: 27
<212> TYPE: DNA
<213> ORGANISM: Artificial Sequence
<220> FEATURE:
<223> OTHER INFORMATION: PCR Fragment

<400> SEQUENCE: 102
cagtcagatc tagagatatc tttactg                                         27

<210> SEQ ID NO 103
<211> LENGTH: 90
<212> TYPE: DNA
<213> ORGANISM: Artificial Sequence
<220> FEATURE:
<223> OTHER INFORMATION: Codon-Optimized HPV6 E2 fragment

<400> SEQUENCE: 103
gaattcagat ctgatatcac catggaggcc atcgccaagc gcctggacgc ctgccaggag     60
cagctgctgg agctgtacga ggagaacagc                                      90

<210> SEQ ID NO 104
<211> LENGTH: 92
<212> TYPE: DNA
<213> ORGANISM: Artificial Sequence
<220> FEATURE:
<223> OTHER INFORMATION: Codon-Optimized HPV6 E2 fragment

<400> SEQUENCE: 104
ccttgtacag cagcacgctc tcgtggcgca tgcacttcca gtgcagcacg tgcttgtgca     60
ggtcggtgct gttctcctcg tacagctcca gc                                   92

<210> SEQ ID NO 105
<211> LENGTH: 96
<212> TYPE: DNA
<213> ORGANISM: Artificial Sequence
<220> FEATURE:
<223> OTHER INFORMATION: Codon-Optimized HPV6 E2 fragment

<400> SEQUENCE: 105
ccacgagagc gtgctgctgt acaaggccaa gcagatgggc ctgagccaca tcggcatgca     60
ggtggtgcct cctctgaagg tgagcgaggc caaggg                               96

<210> SEQ ID NO 106
<211> LENGTH: 103
<212> TYPE: DNA
<213> ORGANISM: Artificial Sequence
<220> FEATURE:
<223> OTHER INFORMATION: Codon-Optimized HPV6 E2 fragment

<400> SEQUENCE: 106
gcagggtcca gggctccatg ctgtactcgg tgcgcagcag gctctcgagg tgcatctgca     60
tctcgatggc gttgtggccc ttggcctcgc tcaccttcag agg                      103

<210> SEQ ID NO 107
<211> LENGTH: 98
<212> TYPE: DNA
```

<213> ORGANISM: Artificial Sequence
<220> FEATURE:
<223> OTHER INFORMATION: Codon-Optimized HPV6 E2 fragment

<400> SEQUENCE: 107

```
cgagtacagc atggagccct ggaccctgca ggagaccagc tacgagatgt ggcagacccc    60
tcccaagcgc tgcttcaaga agcgcggcaa gaccgtgg                            98
```

<210> SEQ ID NO 108
<211> LENGTH: 102
<212> TYPE: DNA
<213> ORGANISM: Artificial Sequence
<220> FEATURE:
<223> OTHER INFORMATION: Codon-Optimized HPV6 E2 fragment

<400> SEQUENCE: 108

```
cgttgtcctg cacgtacacg tcggtccaca ccacgtagtc catggtgttg ttggcgcagc    60
cgtcgaactt cacctccacg gtcttgccgc gcttcttgaa gc                      102
```

<210> SEQ ID NO 109
<211> LENGTH: 102
<212> TYPE: DNA
<213> ORGANISM: Artificial Sequence
<220> FEATURE:
<223> OTHER INFORMATION: Codon-Optimized HPV6 E2 fragment

<400> SEQUENCE: 109

```
ccgacgtgta cgtgcaggac aacgacacct gggtgaaggt gcacagcatg gtggacgcca    60
agggcatcta ctacacctgt ggccagttca agacctacta cg                      102
```

<210> SEQ ID NO 110
<211> LENGTH: 92
<212> TYPE: DNA
<213> ORGANISM: Artificial Sequence
<220> FEATURE:
<223> OTHER INFORMATION: Codon-Optimized HPV6 E2 fragment

<400> SEQUENCE: 110

```
gctgccgtag cacacctccc agtgcttggt gctgccgtac ttctcggcct ccttcacgaa    60
gttcacgtag taggtcttga actggccaca gg                                  92
```

<210> SEQ ID NO 111
<211> LENGTH: 94
<212> TYPE: DNA
<213> ORGANISM: Artificial Sequence
<220> FEATURE:
<223> OTHER INFORMATION: Codon-Optimized HPV6 E2 fragment

<400> SEQUENCE: 111

```
gcactgggag gtgtgctacg gcagcaccgt gatctgcagc ccgctagcg tgagcagcac     60 cacccaggag gtgagcatcc ccgagagcac cacc                                94
```

<210> SEQ ID NO 112
<211> LENGTH: 97
<212> TYPE: DNA
<213> ORGANISM: Artificial Sequence
<220> FEATURE:
<223> OTHER INFORMATION: Codon-Optimized HPV6 E2 fragment

<400> SEQUENCE: 112

```
gcgaggaggg gtctgcacgg cgtcctcctt ggtgctgctg ctcaccaggg tgctggtctg    60
ggcgggagtg taggtggtgc tctcggggat gctcacc                             97
```

-continued

<210> SEQ ID NO 113
<211> LENGTH: 97
<212> TYPE: DNA
<213> ORGANISM: Artificial Sequence
<220> FEATURE:
<223> OTHER INFORMATION: Codon-Optimized HPV6 E2 fragment

<400> SEQUENCE: 113
ggacgccgtg cagacccctc ctcgcaagcg cgcccgcggc gtgcagcaga gcccctgcaa    60
cgccctgtgc gtggcccaca tcggccccgt ggacagc                             97

<210> SEQ ID NO 114
<211> LENGTH: 94
<212> TYPE: DNA
<213> ORGANISM: Artificial Sequence
<220> FEATURE:
<223> OTHER INFORMATION: Codon-Optimized HPV6 E2 fragment

<400> SEQUENCE: 114
ggcgctgctg ttgctgttgt tgcggcgctg gtgctggtcg tggttgttgg tgatcaggtt    60
gtggttgccg ctgtccacgg ggccgatgtg ggcc                                94

<210> SEQ ID NO 115
<211> LENGTH: 95
<212> TYPE: DNA
<213> ORGANISM: Artificial Sequence
<220> FEATURE:
<223> OTHER INFORMATION: Codon-Optimized HPV6 E2 fragment

<400> SEQUENCE: 115
ccgcaacaac agcaacagca gcgccactcc catcgtgcag ttccagggcg agagcaactg    60
cctgaagtgc ttccgctacc gcctgaacga tcgcc                               95

<210> SEQ ID NO 116
<211> LENGTH: 96
<212> TYPE: DNA
<213> ORGANISM: Artificial Sequence
<220> FEATURE:
<223> OTHER INFORMATION: Codon-Optimized HPV6 E2 fragment

<400> SEQUENCE: 116
cgtgcttgtg gggagccttg ctgctggccc agtgccaggt gctgctgatc aggtcgaaca    60
ggtggcggtg gcgatcgttc aggcggtagc ggaagc                              96

<210> SEQ ID NO 117
<211> LENGTH: 95
<212> TYPE: DNA
<213> ORGANISM: Artificial Sequence
<220> FEATURE:
<223> OTHER INFORMATION: Codon-Optimized HPV6 E2 fragment

<400> SEQUENCE: 117
gcagcaaggc tccccacaag cacgccatcg tgaccgtgac ctacgacagc gaggagcagc    60
gccagcagtt cctggacgtg gtgaagatcc ctccc                               95

<210> SEQ ID NO 118
<211> LENGTH: 96
<212> TYPE: DNA
<213> ORGANISM: Artificial Sequence
<220> FEATURE:
<223> OTHER INFORMATION: Codon-Optimized HPV6 E2 fragment

```
<400> SEQUENCE: 118
ctcgagagat ctcccgggtc tagagcttac agcaggtgca ggctcatgaa gcccagcttg      60
tggctgatgg tgggagggat cttcaccacg tccagg                                96

<210> SEQ ID NO 119
<211> LENGTH: 25
<212> TYPE: DNA
<213> ORGANISM: Artificial Sequence
<220> FEATURE:
<223> OTHER INFORMATION: Codon-Optimized HPV6 E2 fragment

<400> SEQUENCE: 119
gaattcagat ctgatatcac catgg                                            25

<210> SEQ ID NO 120
<211> LENGTH: 21
<212> TYPE: DNA
<213> ORGANISM: Artificial Sequence
<220> FEATURE:
<223> OTHER INFORMATION: Codon-Optimized HPV6 E2 fragment

<400> SEQUENCE: 120
gcagggtcca gggctccatg c                                                21

<210> SEQ ID NO 121
<211> LENGTH: 25
<212> TYPE: DNA
<213> ORGANISM: Artificial Sequence
<220> FEATURE:
<223> OTHER INFORMATION: Codon-Optimized HPV6 E2 fragment

<400> SEQUENCE: 121
cgagtacagc atggagccct ggacc                                            25

<210> SEQ ID NO 122
<211> LENGTH: 25
<212> TYPE: DNA
<213> ORGANISM: Artificial Sequence
<220> FEATURE:
<223> OTHER INFORMATION: Codon-Optimized HPV6 E2 fragment

<400> SEQUENCE: 122
gctgccgtag cacacctccc agtgc                                            25

<210> SEQ ID NO 123
<211> LENGTH: 21
<212> TYPE: DNA
<213> ORGANISM: Artificial Sequence
<220> FEATURE:
<223> OTHER INFORMATION: Codon-Optimized HPV6 E2 fragment

<400> SEQUENCE: 123
gcactgggag gtgtgctacg g                                                21

<210> SEQ ID NO 124
<211> LENGTH: 23
<212> TYPE: DNA
<213> ORGANISM: Artificial Sequence
<220> FEATURE:
<223> OTHER INFORMATION: Codon-Optimized HPV6 E2 fragment

<400> SEQUENCE: 124
ggcgctgctg ttgctgttgt tgc                                              23
```

```
<210> SEQ ID NO 125
<211> LENGTH: 22
<212> TYPE: DNA
<213> ORGANISM: Artificial Sequence
<220> FEATURE:
<223> OTHER INFORMATION: Codon-Optimized HPV6 E2 fragment

<400> SEQUENCE: 125
ccgcaacaac agcaacagca gc                                              22

<210> SEQ ID NO 126
<211> LENGTH: 26
<212> TYPE: DNA
<213> ORGANISM: Artificial Sequence
<220> FEATURE:
<223> OTHER INFORMATION: Codon-Optimized HPV6 E2 fragment

<400> SEQUENCE: 126
ctcgagagat ctcccgggtc tagagc                                          26

<210> SEQ ID NO 127
<211> LENGTH: 97
<212> TYPE: DNA
<213> ORGANISM: Artificial Sequence
<220> FEATURE:
<223> OTHER INFORMATION: Codon-Optimized HPV18 E2 fragment

<400> SEQUENCE: 127
gaattcagat ctgatatcac catgcagact cccaaggaga ccctgagcga gcgcctgagc     60
gccctgcagg acaagatcat cgaccactac gagaacg                              97

<210> SEQ ID NO 128
<211> LENGTH: 98
<212> TYPE: DNA
<213> ORGANISM: Artificial Sequence
<220> FEATURE:
<223> OTHER INFORMATION: Codon-Optimized HPV18 E2 fragment

<400> SEQUENCE: 128
cgaagaagat ggcgttctcc cagcggatca gctgccagta ctggatctgg ctgtcgatgt     60
ccttgctgtc gttctcgtag tggtcgatga tcttgtcc                             98

<210> SEQ ID NO 129
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 129
ccgctgggag aacgccatct tcttcgccgc tcgcgagcac gggatccaga ccctgaacca     60
ccaggtggtg cccgcctaca acatcagcaa gagc                                 94

<210> SEQ ID NO 130
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 130
cctcggtctt gtaggcgctc tgggccaggc cctgcagggc catctgcagc tcgatggcct     60
tgtgggcctt gctcttgctg atgttgtagg cggg                                 94
```

<210> SEQ ID NO 131
<211> LENGTH: 91
<212> TYPE: DNA
<213> ORGANISM: Artificial Sequence
<220> FEATURE:
<223> OTHER INFORMATION: Codon-Optimized HPV18 E2 fragment

<400> SEQUENCE: 131
cccagagcgc ctacaagacc gaggactgga ccctgcagga cacctgcgag gagctgtgga    60
acaccgagcc cacccactgc ttcaagaagg g                                   91

<210> SEQ ID NO 132
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 132
gctgtcccag gccacgtagt tcatgcagtt gtccttgttg ccgtcgaagt acacctgcac    60
ggtctggcct cccttcttga agcagtgggt gggc                                94

<210> SEQ ID NO 133
<211> LENGTH: 90
<212> TYPE: DNA
<213> ORGANISM: Artificial Sequence
<220> FEATURE:
<223> OTHER INFORMATION: Codon-Optimized HPV18 E2 fragment

<400> SEQUENCE: 133
gcatgaacta cgtggcctgg gacagcgtgt actacatgac cgacgccggc acctgggaca    60
agaccgccac ctgcgtgagc caccgcggcc                                     90

<210> SEQ ID NO 134
<211> LENGTH: 92
<212> TYPE: DNA
<213> ORGANISM: Artificial Sequence
<220> FEATURE:
<223> OTHER INFORMATION: Codon-Optimized HPV18 E2 fragment

<400> SEQUENCE: 134
ccgtacttct cgcactcgct cttgaactcg atgtagaagg tgttgtagcc ctccttcacg    60
tagtacaggc cgcggtggct cacgcaggtg gc                                  92

<210> SEQ ID NO 135
<211> LENGTH: 94
<212> TYPE: DNA
<213> ORGANISM: Artificial Sequence
<220> FEATURE:
<223> OTHER INFORMATION: Codon-Optimized HPV18 E2 fragment

<400> SEQUENCE: 135
cgagttcaag agcgagtgcg agaagtacgg caacaccggc acctgggagg tgcacttcgg    60
caacaacgtg atcgactgca acgacagcat gtgc                                94

<210> SEQ ID NO 136
<211> LENGTH: 100
<212> TYPE: DNA
<213> ORGANISM: Artificial Sequence
<220> FEATURE:
<223> OTHER INFORMATION: Codon-Optimized HPV18 E2 fragment

<400> SEQUENCE: 136

```
gctgtagggg ctgggagtgt gctgcagctg cttcaccagc tgggtggcgc tcacggtgtc    60
gtcgctggtg ctgcacatgc tgtcgttgca gtcgatcacg                          100

<210> SEQ ID NO 137
<211> LENGTH: 93
<212> TYPE: DNA
<213> ORGANISM: Artificial Sequence
<220> FEATURE:
<223> OTHER INFORMATION: Codon-Optimized HPV18 E2 fragment

<400> SEQUENCE: 137
gcacactccc agcccctaca gcagcaccgt gagcgtgggc accgccaaga cctacggcca    60
gaccagcgcc gccactcgcc ctggccactg cgg                                 93

<210> SEQ ID NO 138
<211> LENGTH: 96
<212> TYPE: DNA
<213> ORGANISM: Artificial Sequence
<220> FEATURE:
<223> OTHER INFORMATION: Codon-Optimized HPV18 E2 fragment

<400> SEQUENCE: 138
gcttgttgtt gccggtggcg gtggcggcgc ccagcagagg gttcacgggc ccgcagtgct    60
gcttctcggc caggccgcag tggccagggc gagtgg                              96

<210> SEQ ID NO 139
<211> LENGTH: 97
<212> TYPE: DNA
<213> ORGANISM: Artificial Sequence
<220> FEATURE:
<223> OTHER INFORMATION: Codon-Optimized HPV18 E2 fragment

<400> SEQUENCE: 139
gccaccgcca ccggcaacaa caagcgccgc aagctgtgca gcggcaacac cactcccatc    60
atccacctga agggcgaccg caacagcctg aagtgcc                             97

<210> SEQ ID NO 140
<211> LENGTH: 97
<212> TYPE: DNA
<213> ORGANISM: Artificial Sequence
<220> FEATURE:
<223> OTHER INFORMATION: Codon-Optimized HPV18 E2 fragment

<400> SEQUENCE: 140
ggcgccggtc cagtgccagg tgctgctgat gtcgcggtag tggtcgctgt gcttgcgcag    60
gcggtaccgc aggcacttca ggctgttgcg gtcgccc                             97

<210> SEQ ID NO 141
<211> LENGTH: 99
<212> TYPE: DNA
<213> ORGANISM: Artificial Sequence
<220> FEATURE:
<223> OTHER INFORMATION: Codon-Optimized HPV18 E2 fragment

<400> SEQUENCE: 141
gcacctggca ctggaccggc gccgggaacg agaagaccgg catcctgacc gtgacctacc    60
acagcgagac ccagcgcacc aagttcctga acaccgtgg                           99

<210> SEQ ID NO 142
<211> LENGTH: 98
<212> TYPE: DNA
```

```
<213> ORGANISM: Artificial Sequence
<220> FEATURE:
<223> OTHER INFORMATION: Codon-Optimized HPV18 E2 fragment

<400> SEQUENCE: 142
ctcgagagat ctcccgggtc tagagcttac atggtcatgt agcccaccag gatctgcacg    60
ctgtcgggga tggccacggt gttcaggaac ttggtgcg                            98

<210> SEQ ID NO 143
<211> LENGTH: 25
<212> TYPE: DNA
<213> ORGANISM: Artificial Sequence
<220> FEATURE:
<223> OTHER INFORMATION: Codon-Optimized HPV18 E2 fragment

<400> SEQUENCE: 143
gaattcagat ctgatatcac catgc                                          25

<210> SEQ ID NO 144
<211> LENGTH: 23
<212> TYPE: DNA
<213> ORGANISM: Artificial Sequence
<220> FEATURE:
<223> OTHER INFORMATION: Codon-Optimized HPV18 E2 fragment

<400> SEQUENCE: 144
cctcggtctt gtaggcgctc tgg                                            23

<210> SEQ ID NO 145
<211> LENGTH: 21
<212> TYPE: DNA
<213> ORGANISM: Artificial Sequence
<220> FEATURE:
<223> OTHER INFORMATION: Codon-Optimized HPV18 E2 fragment

<400> SEQUENCE: 145
cccagagcgc ctacaagacc g                                              21

<210> SEQ ID NO 146
<211> LENGTH: 21
<212> TYPE: DNA
<213> ORGANISM: Artificial Sequence
<220> FEATURE:
<223> OTHER INFORMATION: Codon-Optimized HPV18 E2 fragment

<400> SEQUENCE: 146
ccgtacttct cgcactcgct c                                              21

<210> SEQ ID NO 147
<211> LENGTH: 20
<212> TYPE: DNA
<213> ORGANISM: Artificial Sequence
<220> FEATURE:
<223> OTHER INFORMATION: Codon-Optimized HPV18 E2 fragment

<400> SEQUENCE: 147
cgagttcaag agcgagtgcg                                                20

<210> SEQ ID NO 148
<211> LENGTH: 21
<212> TYPE: DNA
<213> ORGANISM: Artificial Sequence
<220> FEATURE:
<223> OTHER INFORMATION: Codon-Optimized HPV18 E2 fragment

<400> SEQUENCE: 148
```

```
gcttgttgtt gccggtggcg g                                              21

<210> SEQ ID NO 149
<211> LENGTH: 25
<212> TYPE: DNA
<213> ORGANISM: Artificial Sequence
<220> FEATURE:
<223> OTHER INFORMATION: Codon-Optimized HPV18 E2 fragment

<400> SEQUENCE: 149
gccaccgcca ccggcaacaa caagc                                          25

<210> SEQ ID NO 150
<211> LENGTH: 26
<212> TYPE: DNA
<213> ORGANISM: Artificial Sequence
<220> FEATURE:
<223> OTHER INFORMATION: Codon-Optimized HPV18 E2 fragment

<400> SEQUENCE: 150
ctcgagagat ctcccgggtc tagagc                                         26
```